United States Patent
Umezaki et al.

(10) Patent No.: US 10,724,028 B2
(45) Date of Patent: Jul. 28, 2020

(54) LIGAND-BINDING FIBER AND CELL CULTURE SUBSTRATE USING SAID FIBER

(71) Applicant: NISSAN CHEMICAL INDUSTRIES, LTD., Tokyo (JP)

(72) Inventors: Makiko Umezaki, Toyama (JP); Takahiro Kishioka, Toyama (JP); Taito Nishino, Shiraoka (JP); Ayako Aihara, Shiraoka (JP); Shunsuke Iwamoto, Funabashi (JP); Daisuke Sakuma, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 249 days.

(21) Appl. No.: 15/523,157

(22) PCT Filed: Oct. 30, 2015

(86) PCT No.: PCT/JP2015/080649
§ 371 (c)(1),
(2) Date: Apr. 28, 2017

(87) PCT Pub. No.: WO2016/068270
PCT Pub. Date: May 6, 2016

(65) Prior Publication Data
US 2018/0010115 A1   Jan. 11, 2018

(30) Foreign Application Priority Data
Oct. 31, 2014  (JP) ................... 2014-223736

(51) Int. Cl.
| C12N 11/08 | (2020.01) |
| C07K 14/705 | (2006.01) |
| C07K 17/08 | (2006.01) |
| C12M 1/00 | (2006.01) |
| C12N 1/00 | (2006.01) |
| D01F 1/10 | (2006.01) |
| D01F 6/00 | (2006.01) |

(52) U.S. Cl.
CPC ............ *C12N 11/08* (2013.01); *C07K 14/705* (2013.01); *C07K 17/08* (2013.01); *C12M 1/00* (2013.01); *C12N 1/00* (2013.01); *D01F 1/10* (2013.01); *D01F 6/00* (2013.01)

(58) Field of Classification Search
CPC ........ C12N 11/08; C12N 1/00; C07K 14/705; C07K 17/08; C12M 1/00; D01F 1/10; D01F 6/00
USPC ....................................................... 525/500
See application file for complete search history.

(56) References Cited

U.S. PATENT DOCUMENTS

| 7,026,334 B1 | 4/2006 | Takemoto et al. |
| 2003/0195231 A1 | 10/2003 | Takemoto et al. |
| 2004/0063764 A1 | 4/2004 | Takemoto et al. |
| 2004/0077697 A1 | 4/2004 | Koshio et al. |
| 2004/0082626 A1 | 4/2004 | Takemoto et al. |
| 2005/0058692 A1 | 3/2005 | Hai-Quan et al. |
| 2005/0153977 A1 | 7/2005 | Sugasawa et al. |
| 2006/0094694 A1 | 5/2006 | Owada et al. |
| 2007/0082393 A1* | 4/2007 | Lodhi ................. A61L 27/38 435/325 |
| 2010/0040600 A1 | 2/2010 | Yoshikubo et al. |
| 2011/0152455 A1* | 6/2011 | Martin ................ C07D 207/46 525/54.1 |
| 2012/0251925 A1 | 10/2012 | Sasaki |
| 2014/0227780 A1* | 8/2014 | Nishino .............. C12N 5/0644 435/377 |
| 2017/0044491 A1 | 2/2017 | Umezaki et al. |

FOREIGN PATENT DOCUMENTS

| EP | 3106548 A1 | 12/2016 |
| JP | H11-001477 A | 1/1999 |
| JP | H11-152276 A | 6/1999 |
| JP | 2001-097948 A | 4/2001 |
| JP | 2003-066044 A | 3/2003 |
| JP | 2003066044 A * | 3/2003 |
| JP | 2003-238565 A | 8/2003 |
| JP | 2004-529740 A | 9/2004 |
| JP | 2005-102656 A | 4/2005 |
| JP | 2007-325543 A | 12/2007 |
| JP | 2007325543 A * | 12/2007 |
| JP | 4386072 B2 | 12/2009 |
| JP | 2012-052271 A | 3/2012 |
| WO | WO 1999/011262 A1 | 3/1999 |
| WO | WO 2000/035446 A1 | 6/2000 |
| WO | WO 2000/066112 A1 | 11/2000 |
| WO | WO 2001/007423 A1 | 1/2001 |
| WO | WO 2001/017349 A1 | 3/2001 |
| WO | WO 2001/021180 A1 | 3/2001 |
| WO | WO 2001/034585 A1 | 5/2001 |
| WO | WO 2001/039773 A1 | 6/2001 |
| WO | WO 2001/053267 A1 | 7/2001 |
| WO | WO 2001/089457 A2 | 11/2001 |
| WO | WO 2002/049413 A2 | 6/2002 |

(Continued)

OTHER PUBLICATIONS

Chen et al. (A poly(N-isopropylacrylamide-co-N-acryloxysuccinimide-co-2-hydroxyethyl methacrylate) composite hydrogel membrane for urease immobilization to enhance urea hydrolysis rate by temperature swing. Enzyme and Microbial Technology, Jun. 13, 2000, vol. 26, No. 5-6, pp. 359-367) (Year: 2000).*

(Continued)

*Primary Examiner* — Kelechi C Egwim
(74) *Attorney, Agent, or Firm* — Leydig, Voit & Mayer, Ltd.

(57) ABSTRACT

The invention provides a ligand-bonded fiber in which a ligand having affinity for a cell membrane receptor is immobilized on a fiber precursor, and a cell culture substrate capable of repeating ex vivo amplification of a cell expressing a cell membrane receptor by using the ligand-bonded fiber.

15 Claims, No Drawings

(56) References Cited

FOREIGN PATENT DOCUMENTS

| WO | WO 2002/059099 A1 | 8/2002 |
|---|---|---|
| WO | WO 2002/059100 A1 | 8/2002 |
| WO | WO 2002/062775 A1 | 8/2002 |
| WO | WO 2002/085343 A1 | 10/2002 |
| WO | WO 2003/062233 A1 | 7/2003 |
| WO | WO 2004/108683 A1 | 12/2004 |
| WO | WO 2007/012050 A2 | 1/2007 |
| WO | WO 2007/145227 A1 | 12/2007 |
| WO | WO 2011/070893 A1 | 6/2011 |
| WO | WO 2013/051625 A1 | 4/2013 |
| WO | WO 2014/210546 A1 | 12/2014 |
| WO | WO 2015/122478 A1 | 8/2015 |

OTHER PUBLICATIONS

Yanjarappa et al. ("Synthesis of Copolymers Containing an Active Ester of Methacrylic Acid by RAFT: Controlled Molecular Weight Scaffolds for Biofunctionalization. Biomacromolecules", Apr. 19, 2006, vol. 7, No. 5, pp. 1665-1670) (Year: 2006).*

Ma et al. ("Electrospun polyethersulfone affinity membrane: Membrane preparation and performance evaluation", Journal of Chromatography B: Biomedical Sciences & Applications, vol. 877, No. 29, Nov. 1, 2009, pp. 3686-3694). Year: 2009).*

Chen et al., "A poly(N-isopropylacrylamide-co-N-acryloxysuccinimide-co-2- hydroxyethyl methacrylate) composite hydrogel membrane for urease immobilization to enhance urea hydrolysis rate by temperature swing," *Enzyme Microb. Technol.*, 26(5-6): 359-367 (2000).

Yanjarappa et al., "Synthesis of Copolymers Containing an Active Ester of Methacrylic Acid by RAFT: Controlled Molecular Weight Scaffolds for Biofunctionalization," *Biomacromolecules*, 7(5): 1665-1670 (2006).

Intellectual Property Office of Singapore, Written Opinion and Search Report in Singaporean Patent Application No. 11201703407U (dated May 21, 2018).

Ma et al., "Electrospun polyethersulfone affinity membrane: Membrane preparation and performance evaluation," *J. Chromatogr. B*, 877(29): 3686-3694 (2009).

* cited by examiner

LIGAND-BINDING FIBER AND CELL CULTURE SUBSTRATE USING SAID FIBER

CROSS-REFERENCE TO RELATED APPLICATIONS

This patent application is the U.S. national phase of International Patent Application No. PCT/JP2015/080649, filed on Oct. 30, 2015, which claims the benefit of Japanese Patent Application No. 2014-223736, filed on Oct. 31, 2014, the disclosures of which are incorporated herein by reference in their entireties for all purposes.

TECHNICAL FIELD

The present invention relates to a ligand-bonded fiber comprising a ligand having affinity for a cell membrane receptor and a fiber precursor bonded to the ligand, and a cell culture substrate using the ligand-bonded fiber.

BACKGROUND ART

Many cell membrane receptors exist on the cell surface of multicellular organisms, and they receive information given from the outside of the cell and play a role of converting same to information into the cell. Physiological extracellular (intercellular) signal transduction substances (i.e., ligand) targeting cell membrane receptors can be classified into a neurotransmitter, an endocrine substance (hormone), a low molecular substance, a cell proliferation/differentiation factor (cytokine and the like), and a cell adhesion factor, and they respectively have specific affinity for targeting receptors in different secretory formats.

Various studies have conventionally been conducted utilizing the reactivity between cell membrane receptors and ligands. For example, in the treatment of malignant lymphoma and the like, there is a method which includes collecting, from the blood, CD34 positive cells, which are undifferentiated hematopoietic stem cells present in a large amount in the bone marrow and slightly present in blood, and transplanting same. It has been reported that proliferation and differentiation of CD34 positive cells, increase in the engraftment to bone marrow, and recovery of hematopoietic ability can be promoted by using a ligand (antibody) that activates the thrombopoietin (TPO) receptor present on the membrane surface of CD34 positive cells (patent document 1).

However, when a ligand that activates a TPO receptor is taken into the body and the blood concentration of the ligand changes, a different disease may be caused.

On the other hand, a method of immobilizing a ligand (notch ligand delta 1) on a resin has been reported to achieve ex vivo growth of CD34 positive cell while maintaining the undifferentiated state thereof (patent document 2).

However, in the aforementioned method, immobilization of a ligand on general organic resins (polymethyl methacrylate and the like) requires a pre-treatment of the resin, which in turn problematically increases time and labor of operation.

On the other hand, patent document 3 reports a biological function fiber provided with a biomolecule bonded to a polymer.

DOCUMENT LIST

Patent Documents patent document 1: WO 2007/145227
patent document 2: JP-A-2005-102656
patent document 3: National Publication of International Patent Application No. 2004-529740

SUMMARY OF THE INVENTION

Problems to be Solved by the Invention

An object of the present invention is to provide a ligand-bonded fiber wherein a ligand having affinity for a cell membrane receptor is immobilized on a ligand-bonded fiber precursor, and a cell culture substrate capable of repeating ex vivo amplification of a cell expressing a cell membrane receptor by using the ligand-bonded fiber. Particularly, one of the objects of the present invention is to provide a cell culture substrate that can be preferably used for ex vivo culture of cells (e.g., hematopoietic stem cell, hematopoietic progenitor cell, megakaryocyte progenitor cell, megakaryocyte, platelet etc.) that express TPO receptors.

Means of Solving the Problems

The present inventors have conducted intensive studies and found that a ligand-bonded fiber precursor produced by spinning a composition for producing a fiber precursor, which comprises a polymer compound having an active ester group and a hydroxy group in a side chain, a crosslinking agent, an acid compound, and a solvent, has a sufficient organic solvent resistance, can immobilize a ligand having affinity for a cell membrane receptor (e.g., ligand having affinity for TPO receptor etc.). They have further found that the thus-obtained ligand-bonded fiber can be utilized as a cell culture substrate capable of repeating ex vivo amplification of a cell expressing a cell membrane receptor (e.g., TPO receptor etc.).

The present inventors have also found that, since the above-mentioned spinning of a composition for producing a fiber precursor includes spinning a polymer compound having an active ester group and a hydroxy group in a side chain along with a crosslinking agent and an acid compound, hydroxy groups contained in the polymer compound undergo a crosslinking reaction via the crosslinking agent, and polymer compounds are crosslinked. As a result, a fiber precursor having organic solvent resistance and liquid medium resistance is, obtained.

The present inventors have found that the fiber precursor of the present invention expresses more superior organic solvent resistance and liquid medium resistance by applying a heat treatment.

Based on these findings, the present inventors have completed the present invention.

Accordingly, the present invention provides the following.

[1] A ligand-bonded fiber comprising a ligand having affinity for a cell membrane receptor, and a fiber precursor bonded to the ligand, thus forming a ligand-bonded fiber precursor (hereinafter to be referred to as a fiber precursor).

[2] The ligand-bonded fiber of [1], wherein the above-mentioned cell membrane receptor is a thrombopoietin (TPO) receptor.

[3] The ligand-bonded fiber of [1] or [2], wherein the above-mentioned fiber precursor comprises a polymer compound comprising a unit structure represented by the formula (1):

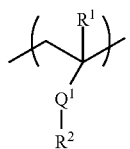

(1)

wherein
  $R^1$ is a hydrogen atom or a methyl group,
  $Q^1$ is an ester bond or amide bond,
  $R^2$ is an alkyl group having 1-10 carbon atoms or an aromatic hydrocarbon group having 6-10 carbon atoms, wherein at least one hydrogen atom is substituted by a hydroxy group, and a unit structure represented by the formula (2):

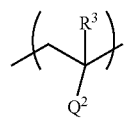

(2)

wherein
  $R^3$ is a hydrogen atom or a methyl group, and
  $Q^2$ is an active ester group.

[4] The ligand-bonded fiber of [3], wherein the above-mentioned ligand has an amino group, and the amino group and the above-mentioned $Q^2$ are bonded.

[5] The ligand-bonded fiber of [3] or [4], wherein the above-mentioned $Q^2$ is represented by the formula (3):

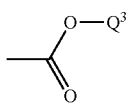

(3)

wherein $Q^3$ is an N-succinimide group, a p-nitrophenyl group or a pentafluorophenyl group.

[6] The ligand-bonded fiber of any one of [3]-[5], wherein the fiber precursor further comprises a crosslinking agent and an acid compound.

[7] The ligand-bonded fiber of any one of [3]-[6], wherein the above-mentioned fiber precursor is produced by spinning a composition for producing a fiber precursor, which composition comprising the above-mentioned polymer compound, a crosslinking agent, an acid compound and a solvent.

[8] The ligand-bonded fiber of [7], wherein the above-mentioned fiber precursor is produced by spinning the above-mentioned composition for producing a fiber precursor, on a surface-treated substrate.

[9] The ligand-bonded fiber of any one of [3]-[8], wherein the above-mentioned polymer compound has a weight average molecular weight of 1,000-1,000,000.

[10] The ligand-bonded fiber of any one of [1]-[9], wherein the above-mentioned fiber precursor is produced by heating at 70-300° C.

[11] The ligand-bonded fiber of any one of [1]-[10], wherein the above-mentioned ligand is a compound represented by the formula (4):

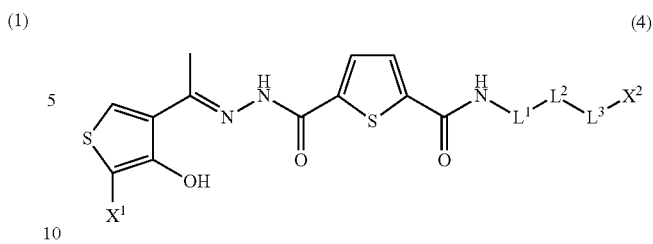

(4)

wherein
  $X^1$ is a 3,4-dichlorophenyl group, a 4-trifluoromethylphenyl group or a 4-t-butylphenyl group,
  $X^2$ is an optionally substituted amino group,
  $L^1$ is a single bond or —$CH_2$—$C_6H_4$—,
  $L^2$ is a single bond or —CONH—, and
  $L^3$ is an alkylene group having 2-6 carbon atoms.

[12] The ligand-bonded fiber of [11], wherein $X^1$ is a 4-t-butylphenyl group, and $X^2$ is an amino group.

[13] A cell culture substrate comprising the ligand-bonded fiber of any one of [1]-[12].

Effect of the Invention

According to the present invention, a superior ligand-bonded fiber that can be utilized as a cell culture substrate capable of repeating ex vivo amplification of a cell expressing a cell membrane receptor (e.g., TPO receptor etc.) and the like can be provided.

DESCRIPTION OF EMBODIMENTS

The ligand-bonded fiber of the present invention is mainly characterized in that it contains a ligand having affinity for a cell membrane receptor, and a fiber precursor bonded to the ligand, thus forming a ligand-bonded fiber precursor (hereinafter to be referred to as a fiber precursor).

1. Fiber Precursor

While the fiber precursor contained in the ligand-bonded fiber of the present invention (precursor of the ligand-bonded fiber of the present invention, i.e., a fiber prior to binding with the ligand) is not particularly limited as long as a ligand having affinity for a cell membrane receptor can bind to, it preferably contains (A) a polymer compound comprising a unit structure represented by the formula (1) and a unit structure represented by the formula (2), more preferably, it is a fiber precursor further containing (B) a crosslinking agent and (C) an acid compound (hereinafter to be also referred to as "the fiber precursor of the present invention").

Each component that can be contained in the fiber precursor of the present invention is described in detail below.

[Component A]

The fiber precursor of the present invention preferably contains, as component A, a polymer compound comprising a unit structure represented by the formula (1) and a unit structure represented by the formula (2) (hereinafter to be also referred to as "the polymer compound of component A" or simply as "component A"). Since the unit structure represented by the formula (1) contained in component A has a hydroxy group in a side chain, when component A is spun together with a crosslinking agent and an acid compound, hydroxy groups undergo a crosslinking reaction via the crosslinking agent, and polymer compounds are crosslinked to give a fiber having organic solvent resistance. In addition, since the unit structure represented by the formula (2) contained in component A has an active ester group in the side chain, it can immobilize the below-mentioned ligand and the like to a polymer compound by a nucleophilic substitution reaction with any amine (particularly, primary alkylamine is preferable).

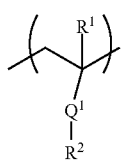
(1)

wherein
$R^1$ is a hydrogen atom or a methyl group,
$Q^1$ is an ester bond or an amide bond,
$R^2$ is an alkyl group having 1-10 carbon atoms or an aromatic hydrocarbon group having 6-10 carbon atoms, wherein at least one hydrogen atom is substituted by a hydroxy group.

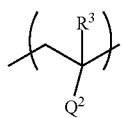
(2)

wherein
$R^3$ is a hydrogen atom or a methyl group, and
$Q^2$ is an active ester group.

The definition of each group of the formula (1) and the formula (2) is described in detail in the following.

$R^1$ is a hydrogen atom or a methyl group.

$Q^1$ is an ester bond or an amide bond, and is preferably an ester bond from the aspect of the solubility of the polymer compound of component A in a solvent.

$Q^2$ is an active ester group. In the present invention, the "active ester group" refers to an ester group wherein a carbonyl group is activated (prone to nucleophilic attack) due to an electron-attractive substituent at one of the ester groups, which is specifically an ester group represented by the formula (3).

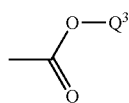
(3)

wherein $Q^3$ is a monovalent organic group (electron-attractive group) that forms an active ester group, which is concretely exemplified by N-succinimide group, p-nitrophenyl group and pentafluorophenyl group, with preference given to N-succinimide group from the aspect of cell affinity.

$R^2$ is an alkyl group having 1-10 carbon atoms or an aromatic hydrocarbon group having 6-10 carbon atoms, wherein at least one hydrogen atom is substituted by a hydroxy group. The alkyl group having 1-10 carbon atoms may be linear or branched chain, and concrete examples thereof include methyl group, ethyl group, propyl group, isopropyl group, butyl group, isobutyl group, sec-butyl group, tert-butyl group, pentyl group, isopentyl group, neo-pentyl group, tert-pentyl group, 1-ethylpropyl group, hexyl group, isohexyl group, 1,1-dimethylbutyl group, 2,2-dimethylbutyl group, 3,3-dimethylbutyl group, 2-ethylbutyl group, octyl group, nonyl group, decyl group and the like. The number of the carbon atoms of the alkyl group is preferably 1-6, more preferably 1-4.

Examples of the "aromatic hydrocarbon group having 6-10 carbon atoms" of the "aromatic hydrocarbon group having 6-10 carbon atoms wherein at least one hydrogen atom is substituted by a hydroxy group" for $R^2$ include phenyl group, 1-naphthyl group, 2-naphthyl group and the like.

$R^2$ is preferably an alkyl group having 1-10 (more preferably 1-6, particularly preferably 1-4) carbon atoms wherein at least one hydrogen atom is substituted by a hydroxy group, or a phenyl group wherein at least one hydrogen atom is substituted by a hydroxy group from the aspects of the efficiency of the crosslinking reaction during fiber precursor production and cell affinity of the produced fiber precursor.

$R^3$ is a hydrogen atom or a methyl group.

In a preferable unit structure represented by the formula (1), $R^1$ is a hydrogen atom or a methyl group, $Q^1$ is an ester bond, $R^2$ is an alkyl group having 1-10 (more preferably 1-6, particularly preferably 1-4) carbon atoms, wherein at least one hydrogen atom is substituted by a hydroxy group, or a phenyl group wherein at least one hydrogen atom is substituted by a hydroxy group.

The unit structure represented by the formula (1) is preferably a unit structure represented by the formula (5).

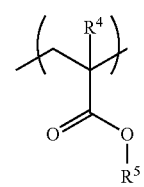
(5)

wherein $R^4$ is as defined for the above-mentioned $R^1$, and $R^5$ is as defined for the above-mentioned $R^2$.

The unit structure represented by the formula (2) is preferably a unit structure represented by the formula (6).

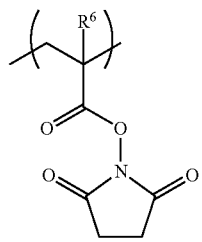
(6)

wherein $R^6$ is a hydrogen atom or a methyl group.

In the polymer compound of component A, the composition ratio of the unit structure represented by the formula (1) and the unit structure represented by the formula (2) is preferably (unit structure represented by the formula (1))/(unit structure represented by the formula (2))=(35-95 mol %)/(5-65 mol %), from the aspects of easiness of synthesis, solubility in solvent, easiness of fiber formation, and effect of immobilization of any amine. The composition ratios of these unit structures can be measured by $^{13}$C-NMR.

While the polymer compound of component A may contain a unit structure other than the unit structure represented by the formula (1) and the unit structure represented by the formula (2) as long as the object of the present invention is not impaired, from the aspect of polymerizability of the polymer compound of component A, the ratio (mol %) of the unit structure represented by the formula (1) is preferably 35-95 mol %, and the ratio (mol %) of the unit structure represented by the formula (2) is preferably 5-65 mol %, each relative to the total unit structure in the polymer compound of component A. In addition, the total (mol %) of the ratio of the unit structure represented by the formula (1) and the ratio of the unit structure represented by the formula (2), each relative to the total unit structure in the polymer compound of component A, preferably exceeds 90 mol %, more preferably not less than 95 mol %, particularly preferably 100 mol %, from the aspect of polymerizability of the polymer compound of component A. The ratio of each unit structure to the total unit structure in the polymer compound of component A can be calculated from the composition ratio of each unit structure measured by $^{13}$C-NMR.

The weight average molecular weight of component A is preferably 1,000-1,000,000, more preferably 5,000-500,000, particularly preferably 10,000-300,000, from the aspects of the organic solvent resistance of the fiber precursor. In the m present invention, the "weight average molecular weight" refers to a molecular weight based on polystyrene, which is measured by gel permeation chromatography (GPC).

Component A can be produced by a method known per se or a method analogous thereto. For example, it can be produced by polymerizing monomers corresponding to the unit structure represented by the formula (1) and monomers corresponding to the unit structure represented by the formula (2) in a suitable solvent (e.g., acetonitrile etc.) by using a suitable polymerization initiator (e.g., dimethyl 2,2'-azobis (isobutyrate) etc.) and the like, but the method is not limited thereto. A commercially available product can also be used.

Examples of the monomer corresponding to the unit structure represented by the formula (1) include 2-hydroxyethyl (meth)acrylate (e.g., compound of CAS number: 868-77-9), 2-hydroxypropyl (meth)acrylate (e.g., compound of CAS number: 923-26-2), 4-hydroxybutyl (meth)acrylate (e.g., compound of CAS number: 2478-10-6), N-hydroxymethyl (meth)acrylamide (e.g., compound of CAS number: 923-02-4), N-(2-hydroxyethyl) (meth)acrylamide (e.g., compound of CAS number: 5238-56-2), N-(2-hydroxypropyl) (meth)acrylamide (e.g., compound of CAS number: 26099-09-2), p-hydroxy (meth)acrylic anilide (e.g., compound of CAS number: 19243-95-9) and the like. Preferred is 2-hydroxyethyl (meth)acrylate or 2-hydroxypropyl (meth) acrylate, and most preferred is 2-hydroxypropyl (meth) acrylate.

In the present invention, the "(meth)acrylate compound" refers to both an acrylate compound and a methacrylate compound. For example, (meth)acrylic acid refers to both acrylic acid and methacrylic acid.

Preferable examples of the monomer corresponding to the unit structure represented by the formula (2) include p-nitrophenyl (meth)acrylate (e.g., compound of CAS number: 16522-41-1), pentafluorophenyl (meth)acrylate (e.g., compound of CAS number: 13642-97-2), N-acrylicoxysuccinimide (compound of CAS number: 38862-24-7), N-succinimidyl methacrylate (compound of CAS number: 38862-25-8), and N-succinimidyl methacrylate is most preferable.

[Component B]

The fiber precursor of the present invention preferably contains, as component B, a crosslinking agent (hereinafter to be also referred to as "the crosslinking agent of component B" or simply as "component B"). Component B when used in combination with the below-mentioned component C crosslinks hydroxy groups of component A via component B itself to impart organic solvent resistance to the fiber precursor.

The crosslinking agent of component B is not particularly limited as long as it can react with a hydroxy group in the presence of an acid, and examples thereof include aminoplast crosslinking agents such as 1,3,4,6-tetrakis(methoxymethyl)glycoluril, 1,3,4,6-tetrakis(butoxy methyl)glycoluril and the like; phenoplast crosslinking agents such as 2,2-bis (4-hydroxy-3,5-dihydroxymethylphenyl)propane and the like; isocyanate crosslinking agents such as hexamethylene diisocyanate and the like; vinylether crosslinking agents such as 1,4-bis(vinyloxy)butane and the like; and the like.

Component B is preferably an aminoplast crosslinking agent, which is preferably 1,3,4,6-tetrakis(hydroxymethyl) glycoluril (CAS number: 5395-50-6), 1,3,4,6-tetrakis (methoxymethyl)glycoluril (CAS number: 17464-88-9), 1,3, 4,6-tetrakis(ethoxymethyl)glycoluril (CAS number: 65952-06-9), 1,3,4,6-tetrakis(1-methylethoxy)glycoluril (CAS number: 508220-69-7), 1,3,4,6-tetrakis(1,1-dimethylethoxy)glycoluril (CAS number: 547744-08-1) or 1,3,4,6-tetrakis(butoxymethyl)glycoluril (CAS number: 15968-37-3), more m preferably 1,3,4,6-tetrakis(methoxymethyl) glycoluril.

Component B may be used alone, or two or more kinds thereof may be used in combination.

The crosslinking agent of component B can be produced by a method known per se or a method analogous thereto. In addition, a commercially available product may also be used.

[Component C]

The fiber precursor of the present invention preferably contains, as component C, an acid compound (hereinafter to be also referred to as "the acid compound of component C" or simply as "component C"). The acid compound may be in the produce of a salt; that is, the term "acid compound" in the present invention is a concept encompassing even a salt. Component C used in combination with component B can promote a crosslinking reaction of hydroxy groups of component A when the crosslinking reaction occurs via component B.

Examples of the acid compound of component C include organic acid compounds such as sulfonic acid compound, carboxylic acid compound and the like; inorganic acid compounds such as hydrochloric acid, phosphoric acid, sulfuric acid, nitric acid, hydrobromic acid and the like, and the like.

Component C is preferably an organic acid compound, more preferably a sulfonic acid compound. Examples of the sulfonic acid compound include p-toluenesulfonic acid, pyridinium p-toluenesulfonate, trifluoromethanesulfonic acid and the like, with preference given to pyridinium p-toluenesulfonate.

Component C may be used alone, or two or more kinds thereof may be used in combination.

The acid compound of component C can be produced by a method known per se or a method analogous thereto. In addition, a commercially available product may also be used.

The fiber precursor of the present invention may contain, as necessary besides components A-C, an additive generally used for a fiber precursor as long as the object of the present invention is not markedly impaired. Examples of the additive include surfactant, rheology adjusting agent, chemical agent, fine particles and the like.

While the kind of the fiber precursor of the present invention is not particularly limited, for example, when the ligand-bonded fiber of the present invention is used for a biocompatible material (e.g., cell culture substrate etc.) and the like, the fiber precursor of the present invention is preferably a fiber precursor having a diameter of nano meter order (e.g., 1-1000 nm) (nanofiber precursor), or micro meter order (e.g., 1-1000 μm) (microfiber precursor) and the like, and a nanofiber precursor is more preferable.

While the diameter (fiber diameter of fiber precursor) of the fiber precursor of the present invention can be appropriately adjusted according to the use of ligand-bonded fiber and the like, it is preferably 1-1000 nm, more preferably 10-1000 nm, from the aspects of the concentration of the below-mentioned composition for fiber precursor production, and easiness of spinning. In the present invention, the diameter of a fiber precursor is measured by a scanning electron microscope (SEM).

The length of the fiber precursor of the present invention is desirably not less than 1000 times that of the above-mentioned fiber precursor.

The weight of the fiber precursor per unit area (fabric weight) is, for example, 7 μg/cm$^2$ or more, preferably 10 μg/cm$^2$ or more.

The production method of the fiber precursor of the present invention is not particularly limited, and a method known per se can be appropriately selected according to the components, kind and the like thereof. For example, when the fiber precursor of the present invention contains the above-mentioned components A-C, the fiber precursor can be produced by spinning a composition for producing a fiber precursor, containing components A-C and a solvent.

The solvent used in the present invention is not particularly limited as long as it can uniformly dissolve or disperse at least the above-mentioned components A-C, and does not react with each component. From the aspects of solubility of components A-C, a polar solvent is preferable.

Examples of the polar solvent include water, methanol, ethanol, 2-propanol, propylene glycol monomethyl ether, acetone, dimethylformamide, dimethylacetamide, N-methylpyrrolidone and the like. Preferred for easy spinning of the composition is a mixed solvent of acetone and dimethylacetamide, and a preferable mixing ratio (wt %) thereof is acetone/dimethylacetamide=(90 wt %-60 wt %)/(10 wt %-40 wt %).

The solvent may be used alone, or two or more kinds thereof may be used in combination.

The content ratio of component A in the composition for producing a fiber precursor is preferably 5-50 wt %, more preferably 10-40 wt %, from the aspects of the production of a fiber precursor having an appropriate thickness.

The content ratio of component B in the composition for producing a fiber precursor is preferably 0.1-5 wt %, more preferably 0.2-4.5 wt %, from the aspects of the reaction efficiency with component A.

The weight ratio of component A and component B (weight of component A/weight of component B) contained in the composition for producing a fiber precursor is preferably 5-65, more preferably 5-25, from the aspects of the reaction efficiency during fiber precursor production.

The content ratio of component C in the composition for producing a fiber precursor is preferably 0.01-1.0 wt %, more preferably 0.05-0.5 wt %, particularly preferably 0.07-0.4 wt %, from the aspects of the crosslinking reaction rate and crosslinking reaction efficiency.

The weight ratio of component A and component C (weight of component A/weight of component C) contained in the composition for producing a fiber precursor is preferably 20-120, more preferably 80-115, from the aspects of the crosslinking reaction rate and crosslinking reaction efficiency.

The composition for producing a fiber precursor may contain, besides components A-C and a solvent, additives similar to those optionally contained in fiber precursors.

The composition for producing a fiber precursor can be prepared by mixing the above-mentioned components A-C and a solvent, or components A-C and a solvent and the above-mentioned additive. The mixing method is not particularly limited, and a method known per se or a method analogous thereto can be used for mixing.

The spinning method of the composition for producing a fiber precursor is not particularly limited as long as it can form a fiber precursor. For example, melt blow method, composite melt spinning method, electrospinning method and the like can be mentioned, and electrospinning method is preferable from the aspect of the fiber forming ability.

Electrospinning method is a known spinning method, and can be performed using a known electrospinning apparatus. Various conditions such as the speed of discharging the composition for producing a fiber precursor of the present invention from the tip of a nozzle (e.g., needle etc.) (discharge speed); application voltage; the distance between the tip of a nozzle discharging the composition for producing a fiber precursor and a substrate (collector part) for receiving same (discharge distance) and the like can be appropriately determined according to the diameter of the fiber precursor to be produced and the like. The discharge speed is generally 0.1-100 μl/min, preferably 0.5-50 μl/min, more preferably 1-20 μl/min. The application voltage is generally 0.5-80 kV, preferably 1-60 kV, more preferably 3-40 kV. The discharge distance is generally 1-60 cm, preferably 2-40 cm, more preferably 3-30 cm.

A substrate (collector part) on which the fiber precursor is formed may or may not be conductive and examples thereof include resin substrates (e.g., polystyrene substrate, acrylic substrate, polycarbonate substrate, polyethylene substrate, vinyl chloride substrate, poly(ethylene terephthalate) substrate etc.), metal substrates (e.g., gold substrate, silver substrate, platinum substrate and the like, including substrates having a surface covered (plated) with a metal), glass substrate, silicon substrate, ceramics substrate and the like. As a cell culture substrate, a resin substrate is preferable from the aspects of breakage resistance of the substrate and easy observation of the cells.

In addition, a substrate on which the fiber precursor is formed may or may not be surface treated. Examples of the surface treatment include metal (e.g., Pt, Pd, Au, Ag, Cu etc.) vapor deposition treatment, UV ozone treatment and the like. When the surface of a substrate with low conductivity (e.g., resin substrate etc.) is subjected to a metal vapor deposition treatment, a large amount of fiber precursor can be formed as compared to that without a metal vapor deposition treatment.

The fiber precursor of the present invention is preferably formed in layers on a substrate, or other structure may be employed.

The fiber precursor of the present invention may be used together with a substrate on which the fiber precursor is formed, or may be used after separation from the substrate. When the fiber precursor of the present invention is used together with the substrate, the fabric weight of the fiber precursor on the substrate (amount of support per unit area on substrate) is generally 7 µg/cm² or more, preferably 10 µg/cm² or more, more preferably 13 µg/cm² or more, most preferably 15 µg/cm² or more. While the upper limit of the fabric weight of the fiber precursor on the substrate is not particularly limited, it is generally 15000 µg/cm².

It is preferable to spin the composition for producing a fiber precursor, and heat the spun fiber precursor at a particular temperature. By heating a spun fiber precursor at a particular temperature, more superior resistance to organic solvents can be expressed.

The temperature for heating a spun fiber precursor is generally 70-300° C. From the aspects of the reactivity of the crosslinking agent of component B, and the heat resistance of the polymer compound of component A, it is preferably 80-250° C., more preferably 90-200° C. When the temperature is less than 70° C., the crosslinking reaction of components A becomes insufficient, and the produced fiber precursor tends to show lower resistance to organic solvents. When it exceeds 300° C., the polymer compound of component A itself undergoes decomposition, dissolution or the like due to the heat, and a fiber precursor cannot be formed.

The heating method of the spun fiber precursor is not particularly limited as long as heating at the above-mentioned heating temperature is possible, and a method known per se or a method analogous thereto can be appropriately used for heating. Specific examples of the heating method include a method using a hot plate, oven or the like under atmosphere, and the like.

While the heating time of the spun fiber precursor can be appropriately determined according to the heating temperature and the like, it is preferably 1 min-48 hr, more preferably 5 min-36 hr, particularly preferably 10 min-24 hr from the aspects of crosslinking reaction rate, and production efficiency.

2. Ligand Having Affinity for Cell Membrane Receptor

A ligand to be contained in the ligand-bonded fiber of the present invention is preferably one having affinity for a cell membrane receptor, and can bind to a fiber precursor. The ligand may also be a synthetic ligand. The "synthetic ligand" here refers to a ligand obtained solely by artificially producing from an organic substance not present in the nature by a chemical synthesis method. Therefore, for example, the synthetic peptide is not a "synthetic ligand" in the context of the present specification.

Examples of the ligand to be used in the present invention include protein, peptide, amino acid, amino acid derivative and saccharides and the like.

The above-mentioned ligand may be naturally occurring, or artificially synthesized or obtained by gene manipulation.

Examples of the aforementioned protein include disease markers such as carcinoembryonic antigen, squamous cell carcinoma related antigen, cytokeratin 19 fragment, sialylated carbohydrate antigen KL-6, natriuretic peptide, troponin, myoglobulin and the like, cell growth factors such as interleukin-1 (IL-1), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), interleukin-13 (IL-13), interleukin-14 (IL-14), interleukin-15 (IL-15), interleukin-18 (IL-18), interleukin-21 (IL-21), interferon-α (IFN-α), interferon-β (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia cell inhibitory factor (LIF), oncostatin M (OM), erythropoietin (EPO), thrombopoietin (TPO), transforming growth factor-α (TGF-α), transforming growth factor-β (TGF-β), macrophage inflammation protein-1α (MIP-1α), epithelial cell growth factor (EGF), fibroblast growth factor-1, 2, 3, 4, 5, 6, 7, 8, or 9 (FGF-1, 2, 3, 4, 5, 6, 7, 8, 9), nerve cell growth factor (NGF), hepatocyte growth factor (HGF), leukemia inhibitory factor (LIF), proteasenexin I, proteasenexin II, platelet-derived growth factor (PDGF), cholinergic differentiation factor (CDF), chemokine, Notch ligand (Delta 1 and the like), Wnt protein, angiopoietin-like protein 2, 3, 5 or 7 (Angpt 2, 3, 5, 7), insulin-like growth factor (IGF), insulin-like growth factor binding protein-1 (IGFBP), Pleiotrophin, insulin, growth hormone and the like, and cell adhesion factors such as collagen I to XIX, fibronectin, vitronectin, laminin-1 to 12, laminin 511, laminin 521, nitrogen, tenascin, thrombospondin, von Willebrand (von Willebrand) factor, osteopontin, fibrinogen, various elastin, various proteoglycan, various cadherin, desmocollin, desmoglein, various integrin, E-selectin, P-selectin, L-selectin, immunoglobulin superfamily, matrigel, poly-D-lysine, poly-L-lysine and the like, various antibodies such as IgG, IgM, IgA, IgD, IgE and the like and the like.

Examples of the aforementioned peptide include peptides such as angiotensin I to IV, bradykinin, fibrinopeptide, natriuretic peptide, urodilatin, guanylin, endothelin 1 to 3, salusin, urotensin, oxytocin, neurophysin, vasopressin, adrenocorticotropic hormone, melanocyte-stimulating hormone, endorphin, lipotropin, urocrtin 1 to 3, luteinizing hormone releasing hormone, growth hormone releasing hormone, somatostatin, cortistatin, prolactin releasing peptide, metastin, tachykinin, substance P, neurokinin, endokinin, neurotension, neuromedin, xenin, ghrelin, obestatin, melanin-concentrating hormone, orexin, neuropeptide, dynorphin, neoendorphin, endomorphine, nociceptin, pyroglutamylated RF amide peptide, galanin, gastrin, cholecystokinin, secretin, relaxin, glucagon, glicentin, adrenomedullin, amylin, calcitonin, parathyroid hormone, defensin, thymosin, YIGSR peptide and the like.

Examples of the aforementioned amino acid include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, cystine, hydroxyproline, hydroxylysine, dihydroxyphenylalanine, thyroxine, phosphoserine, desmosine, β-alanine, sarcosine, ornithine, creatine, γ-amino butyric acid, theanine, kainic acid, domoic acid, ibotenic acid and the like.

Examples of the aforementioned amino acid derivative include serotonin, noradrenaline, adrenaline, tyramine (compound of CAS number: 51-67-2), dopamine (compound of CAS number: 51-61-6) and the like.

Examples of the aforementioned saccharides include D-glucosamine, D-galactosamine, neuraminic acid, hyaluronic acid, chondroitin sulfate, heparan sulfate, heparin and the like.

In the present invention, a chemical substance other than protein, peptide, amino acid, amino acid derivative and saccharides may also be used as a ligand. Examples of such chemical substance include primary amines such as 2-dimethylaminoethylamine (compound of CAS number: 108-00-9), N-(2-hydroxyethyl)ethylenediamine (compound of CAS number: 111-41-1), N-(2-aminoethyl)piperazine (compound of CAS number: 140-31-8), 4-(2-aminoethyl)morpholine (compound of CAS number: 2038-03-1), 1-(2-aminoethyl)-2-imidazolidinone (compound of CAS number: 6281-42-1), tryptamine (compound of CAS number: 61-54-1), histamine dihydrochloride (compound of CAS number: 56-92-8) and the like; primary diamines such as ethylenediamine dihydrochloride (compound of CAS number: 333-18-6), 1,6-diaminohexane (compound of CAS number: 124-09-4), N,N'-bis(aminopropyl)piperazine (compound of CAS number: 7209-38-3) and the like.

In the present invention, a ligand having affinity for a thrombopoietin (TPO) receptor may also be used as a ligand. Examples of the ligand having affinity for a thrombopoietin (TPO) receptor include the compounds described in JP-A-11-1477, JP-A-11-152276, WO 01/07423, WO 01/53267, WO 02/059099, WO 02/059100, WO 00/35446, WO 00/66112, WO 01/34585, WO 01/17349, WO 01/39773, WO 01/21180, WO 01/89457, WO 02/49413, WO 02/085343, JP-A-2001-97948, WO 99/11262, WO 02/062775, WO 03/062233, JP-A-2003-238565 and the like. Also, the compounds represented by the following formulas (7)-(15) may be used as a ligand having affinity for a thrombopoietin (TPO) receptor.

(7)

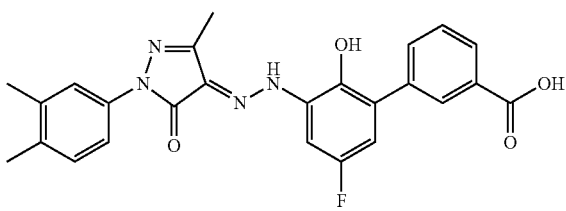

(8)

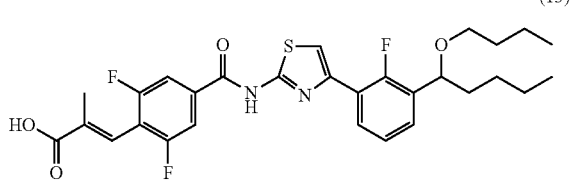

(9)

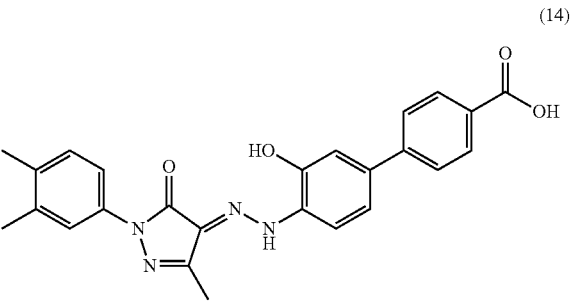

(10)

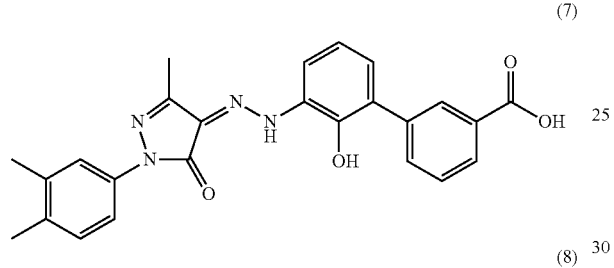

(11)

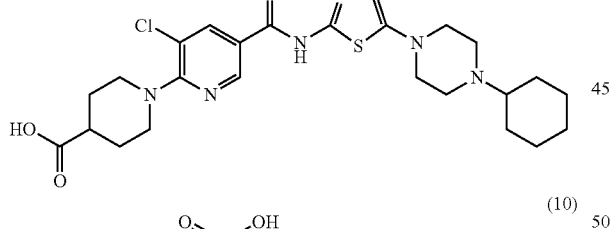

(12)

(13)

(14)

(15)

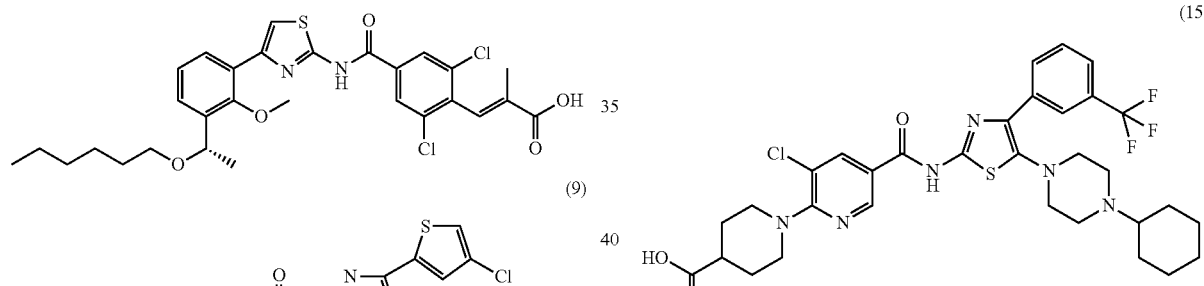
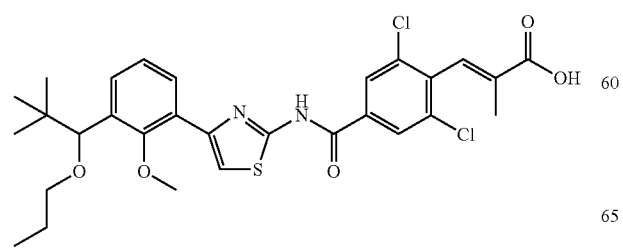

While the binding foam of the fiber precursor of the present invention and a ligand is not particularly limited as long as they are bonded, in one embodiment, when the fiber precursor of the present invention contains a polymer compound of component A and the ligand has an amino group, the amino so group of the ligand and $Q^2$ of component A can be bonded by a nucleophilic substitution reaction.

Specific examples of the ligand having an amino group include a compound obtained by converting carboxylic acid of the compound exemplified above to carboxylic acid amide and aminating the carboxylic acid amide by a Hofmann rearrangement reaction and the like.

In addition, as a ligand to be used in the present invention, a compound exemplified above wherein a part of the substituent is aminated according to a method known per se may be used as the ligand of the present invention.

A particularly preferable one embodiment of the ligand having an amino group is a compound represented by the formula (4) (hereinafter to be also referred to as "compound (4)").

(4)

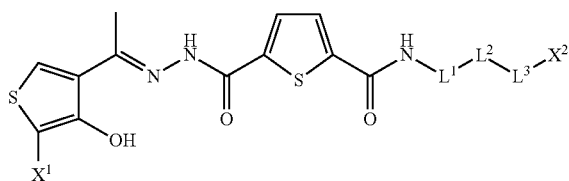

wherein
$X^1$ is a 3,4-dichlorophenyl group, a 4-trifluoromethylphenyl group or a 4-t-butylphenyl group,
$X^2$ is an optionally substituted amino group,
$L^1$ is a single bond or —CH$_2$—C$_6$H$_4$—,
$L^2$ is a single bond or —CONH—, and
$L^3$ is an alkylene group having 2-6 carbon atoms.

The definition of each group of the formula (4) is described in detail in the following.

$X^1$ is a 3,4-dichlorophenyl group, a 4-trifluoromethylphenyl group or a 4-t-butylphenyl group, preferably a 4-t-butylphenyl group.

$X^2$ is an optionally substituted amino group. In the present specification, "optionally substituted" means optionally having one or more substituent(s) unless particularly defined, and examples of the "substituent" include methyl group, ethyl group, n-propyl group, isopropyl group, t-butyl group, allyl group, phenyl group, benzyl group and the like.

$X^2$ is preferably an amino group.

$L^1$ is a single bond or —CH$_2$—C$_6$H$_4$—, preferably, a single bond.

$L^2$ is a single bond or —CONH—, preferably, a single bond.

$L^3$ is an alkylene group having 2-6 carbon atoms. The alkylene group having 2-6 carbon atoms may be a straight chain or branched or cyclic and, for example, ethylene group, n-propylene group, tetramethylene group, pentamethylene group, hexamethylene group, dimethylmethylene group, methylethylene group, dimethylethylene group, dimethylpropylene group, cyclopropylene group, cyclohexylene group and the like can be mentioned. Of these, an alkylene group having 2-4 carbon atoms is preferable, and an alkylene group having 2-3 carbon atoms is more preferable.

A preferable compound (4) is compound (4) wherein
$X^1$ is a 4-t-butylphenyl group,
$X^2$ is preferably an amino group,
$L^1$ is a single bond or —CH$_2$—C$_6$H$_4$— (preferably, a single bond),
$L^2$ is a single bond or —CONH— (preferably, a single bond),
$L^3$ is an alkylene group having 2-6 (preferably 2-4, more preferably 2-3) carbon atoms.

Specific examples of preferable compound (4) include the compounds represented by the following formulas (16)-(18) and the like.

(16)

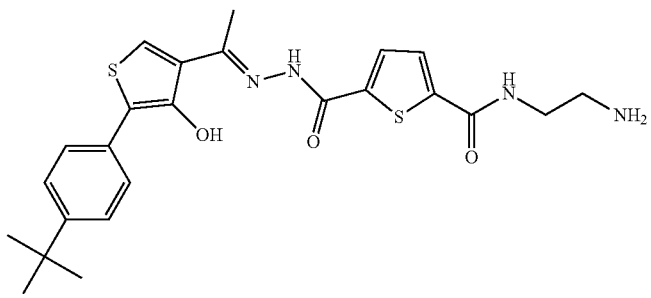

(17)

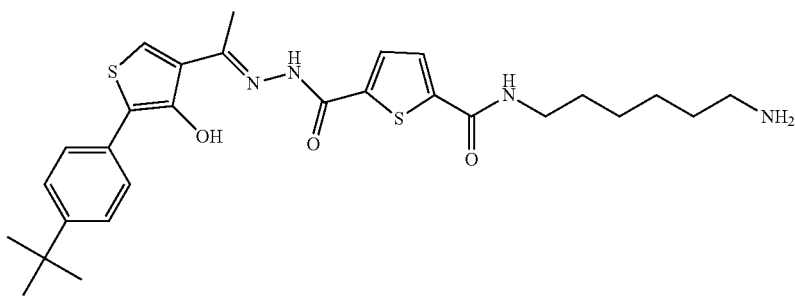

(18)

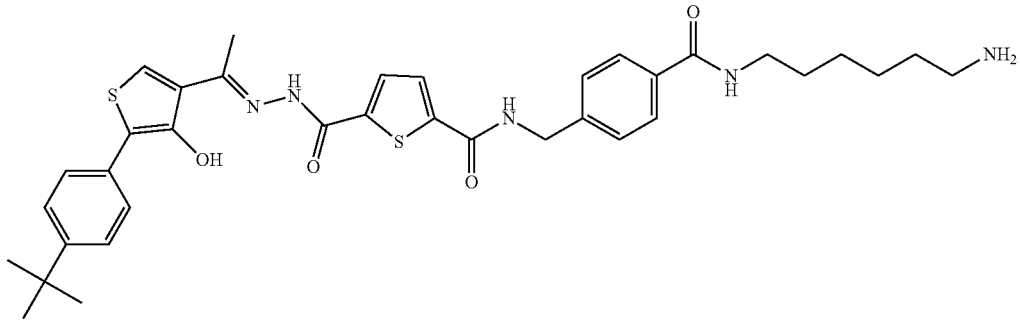

Compound (4) can be produced by the method described in, for example, JP-B-4386072, or a method analogous thereto.

3. Production of Ligand-Bonded Fiber (Immobilization of Ligand to Fiber Precursor)

In the present invention, while the binding form of the fiber precursor and a ligand is not particularly limited as long as they are bonded, in one embodiment, when a fiber precursor having an active ester group (e.g., the fiber precursor of the present invention etc.) is used, a ligand having affinity for a cell membrane receptor can be immobilized on the aforementioned fiber precursor by a reaction between an active ester group present in the fiber precursor and a ligand. An active ester group reacts with a free amino group under neutral conditions. The basicity of amine is stronger in alkylamine than aromatic amine, and alkylamine is more suitable for reaction with active ester. In the case of amine having low water-solubility, it is preferable to perform reaction by dissolving same in an organic solvent such as ethanol, dimethyl sulfoxide and the like. When the fiber precursor of the present invention is used, the reaction between the active ester group and the ligand can be performed during preparation of a composition for producing a fiber precursor. It may be performed after production of a fiber precursor by spinning a composition for producing a fiber precursor, or after a heat treatment of the fiber precursor. The reaction conditions are preferably 0° C.-80° C. for 1-48 hr, further preferably 0° C.-60° C. for 1-24 hr, most preferably 0° C.-50° C. for 1-24 hr.

While the diameter of the ligand-bonded fiber of the present invention can be appropriately adjusted according to the use thereof and the like, it is preferably 1-1000 nm, more preferably 10-1000 nm. In the present invention, the diameter of a ligand-bonded fiber is measured by a scanning electron microscope (SEM).

In addition, the length of the ligand-bonded fiber of the present invention is desirably not less than 1000 times that of the above-mentioned fiber precursor.

The ligand-bonded fiber of the present invention may be used while being supported on the substrate. In this case, the fabric weight of the ligand-bonded fiber on the substrate (amount of support per unit area on substrate) is generally 7 μg/cm$^2$ or more, preferably 10 μg/cm$^2$ or more, more preferably 13 μg/cm$^2$ or more, most preferably 15 μg/cm$^2$ or more. While the upper limit of the fabric weight of the ligand-bonded fiber on the substrate is not particularly limited, it is generally 15000 μg/cm$^2$.

Generally, the fabric weight of the fiber precursor is almost the same as that of the ligand-bonded fiber (within error range).

While the use of the ligand-bonded fiber of the present invention is not particularly limited, the ligand-bonded fiber of the present invention is particularly suitable as a cell m culture substrate (e.g., material of cell culture scaffold etc.), since it has superior resistance to organic solvents and has sufficient function as cell culture substrate.

4. Cell Culture Substrate

The cell culture substrate of the present invention is mainly characterized in that it contains the ligand-bonded fiber of the present invention. In the present invention, the "cell culture substrate" refers to a material permitting selective culture of particular cells alone without exerting an adverse influence on the cell.

Examples of the cell culture substrate of the present invention include a cell culture substrate obtained by spraying the ligand-bonded fiber of the present invention on glass, metal or plastic such as polystyrene (e.g., 6 well flat-bottom microplate etc.), a culture bag introduced with the ligand-bonded fiber of the present invention and the like The "cell" to be cultured using the cell culture substrate of the present invention is the most basic unit constituting animals or plants, and has the cytoplasm and various organelles as the factors thereof in the cell membrane. In this case, the nucleus enclosing the DNA may or may not be included in the intracellular portion.

The cell culture substrate of the present invention can be used, for example, for culturing cells derived from animals. The cells derived from animals in the present invention include reproductive cells such as spermatozoon, ovum and the like, somatic cells constituting the body, stem cells (including pluripotent stem cell and the like), progenitor cells, cancer cells separated from the body, cells isolated from the body, which acquired immortalizing ability and are stably maintained outside the body (namely, cell line (including cancer cell line)), cells isolated from the body and artificially modified genetically, cells isolated from the body and having artificially exchanged nucleus and the like.

Examples of the cells constituting the body include, but are not limited to, fibroblast, bone marrow cell, B lymphocyte, T lymphocyte, neutrophil, red blood cell, platelet, macrophage, monocyte, osteocyte, bone marrow cell, pericyte, dendritic cell, keratinocyte, adipocyte, mesenchyme cell, epithelial cell, epidermal cell, endothelial cell, vascular endothelial cell, hepatocyte, chondrocyte, cumulus cell, nerve system cell, glial cell, neuron, oligodendrocyte, microglia, astrocyte, cardiocyte, esophagus cell, myocytes (e.g., smooth muscle cell or skeleton muscle cell), pancreas beta cell, melanocyte, hematopoietic progenitor cell (e.g., CD34 positive cell derived from cord blood), mononuclear cell and the like. The somatic cell can be harvested from any tissue, for example, skin, kidney, spleen, adrenal gland, liver, lung, ovary, pancreas, uterus, stomach, colon, small intestine, large intestine, bladder, prostate, testis, thymus, muscle, bond tissue, bone, cartilage, blood vessel tissue, blood (including cord blood), bone marrow, heart, eye, brain, neural tissue and the like.

Stem cell is a cell simultaneously having an ability to replicate itself and an ability to differentiate into other multiple lineages of cells. Examples thereof include, but are not limited to, embryonic stem cells (ES cell), embryonic tumor cell, embryonic germ cell, induced pluripotent stem cell (iPS cell), neural stem cell, hematopoietic stem cell, mesenchymal stem cell, liver stem cell, pancreas stem cell, muscle stem cell, reproductive stem cell, intestinal stem cell, cancer stem cell, hair follicle stem cell, and the like. Examples of the pluripotent stem cell include ES cell, embryonic germ cell, iPS cell and the like from the aforementioned stem cells.

Progenitor cell is a cell in the stage of differentiation from the aforementioned stem cell into a specific somatic cell or reproductive cell. Cancer cell is a cell derived from a somatic cell, which acquired infinite proliferative capacity.

Examples of the cell line include, but are not limited to, HEK293 (human embryonic kidney cell), MDCK, MDBK, BHK, C-33A, AE-1, 3D9, Ns0/1, NIH3T3, PC12, S2, Sf9, Sf21, High Five (registered trade mark), Vero and the like.

Examples of the cancer cell line include, but are not limited to, HBC-4, BSY-1, BSY-2, MCF-7, MCF-7/ADR RES, HS578T, MDA-MB-231, MDA-MB-435, MDA-N, BT-549, T47D as human breast cancer cell lines, HeLa as a human uterus cervix cancer cell line, A549, EKVX, HOP-62, HOP-92, NCI-H23, NCI-H226, NCI-H322M, NCI-H460, NCI-H522, DMS273, DMS114 as human lung cancer cell lines, Caco-2, COLO-205, HCC-2998, HCT-15, HCT-116, HT-29, KM-12, SW-620, WiDr as human large intestine cancer cell lines, DU-145, PC-3, LNCaP as human prostate cancer cell lines, U251, SF-295, SF-539, SF-268, SNB-75, SNB-78, SNB-19 as human central nervous system cancer cell lines, OVCAR-3, OVCAR-4, OVCAR-5, OVCAR-8, SK-OV-3, IGROV-1 as human ovarian cancer cell lines, RXF-631L, ACHN, UO-31, SN-12C, A498, CAKI-1, RXF-393L, 786-0, TK-10 as human kidney cancer cell lines, MKN45, MKN28, St-4, MKN-1, MKN-7, MKN-74 as human gastric cancer cell lines, LOX-IMVI, LOX, MALME-3M, SK-MEL-2, SK-MEL-5, SK-MEL-28, UACC-62, UACC-257, M14 as skin cancer cell lines, CCRF-CRM, K562, MOLT-4, HL-60 TB, RPMI8226, SR, UT7/TPO, Jurkat as leukemia cell lines, and the like.

Of these cells, examples of the cell to be cultured using a cell culture substrate (e.g., cell culture scaffold material etc.) containing the ligand-bonded fiber of the present invention using a ligand having affinity for TPO receptor include hematopoietic stem cell, hematopoietic progenitor cell, megakaryocyte progenitor cell, megakaryocyte, platelet, UT7/TPO cell and the like expressing TPO receptors.

The cell culture substrate of the present invention can be produced using the ligand-bonded fiber of the present invention as one of the starting materials and according to a method known per se or a method analogous thereto.

EXAMPLES

While specific examples of the present invention are explained below, the present invention is not limited in any way by the examples.

[Measurement of Weight Average Molecular Weight of Polymer Compound 1]

The weight average molecular weight of the following polymer compound 1 is measured by gel permeation chromatography (GPC). The apparatus used for the measurement and measurement conditions are as follows.

apparatus: TOSOH HLC-8320GPC system
column: Shodex (registered trade mark) KF-803L, KF-802 and KF-801
column temperature: 40° C.
eluent: DMF
flow rate: 0.6 ml/min
detector: RI
standard sample: polystyrene

[C-NMR Measurement of Polymer Compound 1]

The composition ratio of the unit structure of the following polymer compound 1 is measured by $^{13}$C-NMR. The apparatus and conditions used for the measurement and analysis were as follows.

apparatus: JEOL Ltd. JNM-ECA500, Delta V5.0
measurement nucleus: $^{13}$C gated decoupling
cumulated number: 18000
measurement temperature: room temperature
detection peak: 69-71 ppm (derived from HPMA), 25-27 ppm (derived from NSuMA)
measurement solvent: deuterated dimethyl sulfoxide (DMSO-$d_6$), 750 uL
sample amount: 0.1 g
mitigation reagent: chrome(III) acetylacetonate, 4 mg

[$^1$H-NMR Measurement of Ligand Compound]

Ligand compound was identified by $^1$H-NMR. The conditions were as follows.

apparatus: Varian NMR System 400 NB (400 MHz)
measurement solvent: $CDCl_3$
standard substance: tetramethylsilane (TMS) (δ0.0 ppm, $^1$H)

Synthetic Example 1: Polymer Compound 1

2-Hydroxypropyl methacrylate (HPMA; manufactured by Tokyo Chemical Industry Co., Ltd.) (18.37 g), N-succinimidyl methacrylate (NSuMA; manufactured by Tokyo Chemical Industry Co., Ltd.) (10.00 g), and dimethyl 2,2'-azobis (2-methylpropionate) (MAIB; manufactured by Wako Pure Chemical Industries, Ltd.) (0.03 g) were dissolved in acetonitrile (66.25 g), and added dropwise under a nitrogen atmosphere to acetonitrile (47.32 g) heated under reflux. After completion of the dropwise addition, the mixture was reacted for 18 hr while maintaining heating under reflux. The reaction mixture was added dropwise to diethyl ether to precipitate polymer. The polymer was taken out, and dried under reduced pressure to give polymer compound 1 (19.9 g). The weight average molecular weight of the polymer compound 1 was 235,000 based on polystyrene. The composition ratio measured by $^{13}$C-NMR was HPMA/NSuMA=63 mol %/37 mol %.

Synthetic Example 2: Synthesis of Ligand Compound [4]

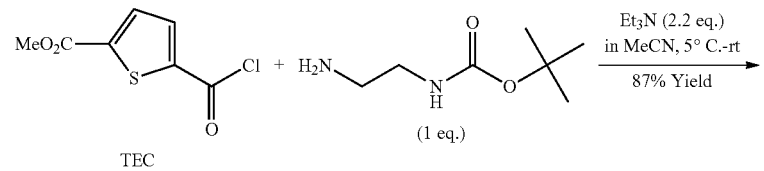

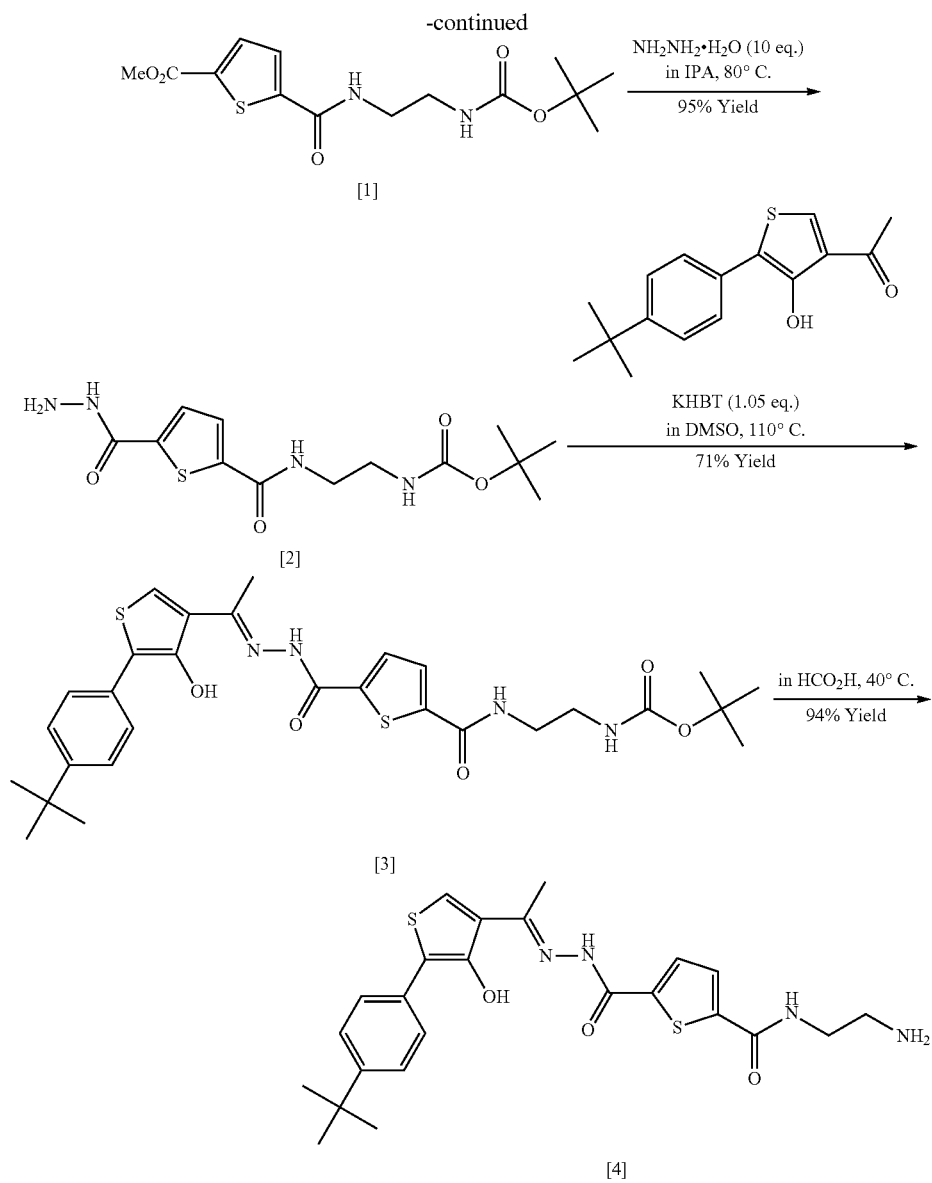

<Synthesis of Compound [1]>

In a 50 ml four-necked flask provided with a magnetic stirrer, methyl 5-(chlorocarbonyl)thiophene-2-carboxylate (TEC) (1.00 g, 4.89 mmol) and acetonitrile (12 g) were charged, and the inside temperature was maintained at 5° C. To the mixture were added dropwise a solution of N-(tert-butoxycarbonyl)-1,2-diaminoethane (0.783 g, 4.89 mmol) and triethylamine (1.088 g, 10.75 mmol) in acetonitrile (8 g), and the mixture was stirred at room temperature for 17 hr. To the reaction mixture were added ethyl acetate (30 g) and pure water (30 g) to partition the mixture, and the organic phase was recovered. To the organic phase was added sodium sulfate (5 g), and the mixture was stood for 30 min and filtered. Then, the filtrate was dried by concentration to give compound [1] (1.39 g, 4.23 mmol) (yield: 87%, property: pale brown solid).

$^1$H-NMR (400 MHz) in CDCl$_3$:1.43 ppm (s, 9H), 3.37-3.44 ppm (m, 2H), 3.51-3.56 ppm (m, 2H), 3.90 ppm (s, 3H), 4.99-5.11 ppm (m, 1H), 7.32 ppm (d, J=3.5 Hz, 1H), 0.98-1.12 ppm (m, 1H), 8.03 ppm (d, J=3.5 Hz, 1H)

<Synthesis of Compound [2]>

In a 50 ml four-necked flask provided with a magnetic stirrer, compound [1] (1.36 g, 4.14 mmol), hydrazine monohydrate (2.073 g, 41.42 mmol), and 2-propanol (23.20 g) were charged, and the mixture was stirred at inside temperature 80° C. for 6 hr. Then, the reaction mixture was dried by concentration under reduced pressure to give compound [2] (1.29 g, 3.93 mmol) (yield: 95%, property: yellow crystal).

$^1$H-NMR (400 MHz) in d6-DMS0:1.37 ppm (s, 9H), 3.07 ppm (q, J=6.3 Hz, 2H), 3.24 ppm (q, J=6.3 Hz, 2H), 4.26-4.78 ppm (br, 2H), 6.93 ppm (t, J=5.5 Hz, 1H), 7.63-7.67 ppm (m, 2H), 8.62 ppm (t, J=5.5 Hz, 1H), 9.78-10.06 ppm (br, 1H)

<Synthesis of Compound [3]>

In a 50 ml four-necked flask provided with a magnetic stirrer, compound [2] (1.29 g, 3.93 mmol), KHBT (synthesized according to the method described in WO 2004/108683 or US-B-2006/094694) (1.13 g, 4.13 mmol), and dimethyl sulfoxide (11.90 g) were charged, and the mixture was stirred at inside temperature 110° C. for 5 hr. To the reaction mixture was added pure water (50 g), and the precipitated crystals were suction filtered under reduced pressure. The crystals were washed with diisopropyl ether (6 g), and dried under reduced pressure to give compound [3] (1.63 g, 2.79 mmol) (yield: 71%, property: yellow crystal).

$^1$H-NMR (400 MHz) in d6-DMS0:1.30 ppm (s, 9H), 1.38 ppm (s, 9H), 2.48 ppm (s, 3H), 3.08-3.14 ppm (m, 2H), 3.22-3.33 ppm (m, 2H), 6.94 ppm (t, J=5.5 Hz, 1H), 7.42 ppm (d, J=8.4 Hz, 2H), 7.69 ppm (d, J=8.4 Hz, 2H), 7.77 ppm (d, J=3.7 Hz, 1H), 7.98 ppm (s, 1H), 8.00 ppm (d, J=3.7 Hz, 1H), 8.72 ppm (t, J=5.7 Hz, 1H), 11.24-11.55 ppm (br, 1H), 11.98-12.22 ppm (br, 1H)

<Synthesis of Compound [4]>

In a 50 ml four-necked flask provided with a magnetic stirrer, compound [3] (1.38 g, 2.35 mmol) and 98% formic acid (14.00 g) were charged, and the mixture was stirred at inside temperature 40° C. for 1 hr. Under reduced pressure, formic acid was evaporated from the reaction mixture, diisopropyl ether (7 g) and tetrahydrofuran (1.4 g) were added, and the precipitated crystals were suction filtered under reduced pressure. Then, the crystals were dried under reduced pressure to give compound [4] (1.07 g, 2.21 mol) (yield: 94%, property: yellow crystal).

$^1$H-NMR (400 MHz) in d6-DMS0:1.30 ppm (s, 9H), 2.47 ppm (s, 3H), 2.96 ppm (t, J=6.0 Hz, 2H), 3.48 ppm (q, J=5.7 Hz, 2H), 7.41 ppm (d, J=8.6 Hz, 2H), 7.70 ppm (d, J=8.6 Hz, 2H), 7.82 ppm (d, J=4.0 Hz, 1H), 7.93 ppm (s, 1H), 7.96 ppm (d, J=4.0 Hz, 1H), 8.32 ppm (s, 1H), 9.22 ppm (t, J=5.1 Hz, 1H), 12.05-12.95 (br, 1H)

<Preparation of Composition for Producing Fiber Precursor Solution>

(Composition 1 for Producing a Fiber Precursor)

Polymer compound 1 (1.70 g), 1,3,4,6-tetrakis (methoxymethyl)glycoluril (0.34 g), pyridinium p-toluene-sulfonate (0.017 g), dimethylacetamide (1.57 g), and acetone (4.50 g) were mixed, and the mixture was stirred by a mix rotor VMR-5 (manufactured by AS ONE Corporation) at 100 rpm until dissolution to give a composition 1 for producing fiber precursor. The content ratio of polymer compound 1 in the composition 1 for producing fiber precursor 1 was about 21 wt %.

[Production of Fiber Precursor by Electric Field Spinning Method]

A fiber precursor was produced by the electric field spinning method using Esprayer ES-2000 (manufactured by Fuence Co., Ltd.). A composition 1 for producing fiber precursor was filled in a 1 ml lock-type glass syringe (manufactured by AS ONE Corporation), and a lock-type metallic needle 24G with needle length of 13 mm (manufactured by Musashi engineering) was attached. The distance from the needle tip to the substrate for receiving the fiber (discharge distance) was set to 20 cm. The applied voltage was 25 kV, and the discharge speed was 10 μl/min.

[Confirmation Method of Fiber Precursor Form]

The fiber precursor form was confirmed by vapor depositing Pt—Pd on the fiber precursor for 1 min by ion sputter (E-1030, manufactured by Hitachi High-Technologies Corporation), and observing same under a scanning electron microscope (SEM) (S-4800, manufactured by Hitachi High-Technologies Corporation) at magnification ×10,000.

[Measurement Method of Fiber Diameter of Fiber Precursor]

The fiber diameter of fiber precursor (thickness of fiber precursor) was measured using a scanning electron microscope (SEM) (S-4800, manufactured by Hitachi High-Technologies Corporation), by taking and preserving images at magnification ×10,000 and measuring by the attached length measuring tool.

[Surface Treatment A of Polystyrene (PSt) Substrate]

One surface of a Φ30 mm polystyrene (PSt) substrate produced from "PLABAN" (trade name; thickness 0.2 mm) manufactured by ACRYSUNDAY Co., Ltd. was Pt—Pd vapor deposited for 30 sec by an ion sputter (E-1030, manufactured by Hitachi High-Technologies Corporation).

[Surface Treatment B of Polystyrene (PSt) Substrate]

One surface of a Φ30 mm polystyrene (PSt) substrate produced from "PLABAN" (trade name; thickness 0.2 mm) manufactured by ACRYSUNDAY Co., Ltd. was treated by UV ozone cleaner UV253E (manufactured by Filgen, Inc.) for 10 min.

Example 1

The composition 1 for producing a fiber precursor was spun by the electric field spinning method, sprayed for 20 min on the Φ30 mmPSt substrate subjected to the above-mentioned surface treatment A, and heat treated at 80° C. for 48 hr. The obtained fiber precursor (fiber precursor 1) was washed with ethanol and air dried, and the form of the fiber precursor 1 was confirmed by a scanning electron microscope (SEM). The fiber diameter of the fiber precursor 1 was about 700 nm. Ligand compound [4] was immobilized on the fiber precursor 1 by the below-mentioned method to give a ligand compound [4]-immobilized fiber precursor 1 (ligand-bonded fiber 1).

Example 2

In the same manner as in Example 1 except that a Φ30 mmPSt substrate that underwent the above-mentioned surface treatment B was used instead of the Φ30 mm PSt substrate that underwent the above-mentioned surface treatment A, a fiber precursor 2 was obtained. The fiber diameter of the fiber precursor 2 was about 700 nm. Ligand compound [4] was immobilized on the fiber precursor 2 by the below-mentioned method to give a ligand compound [4]-immobilized fiber precursor 2 (ligand-bonded fiber 2).

Example 3

In the same manner as in Example 1 except that an untreated Φ30 mmPSt substrate was used instead of the Φ30 mm PSt substrate that underwent the above-mentioned surface treatment A, a fiber precursor 3 was obtained. The fiber diameter of the fiber precursor 3 was about 570 nm. Ligand compound [4] was immobilized on the fiber precursor 3 by the below-mentioned method to give a ligand compound [4]-immobilized fiber precursor 3 (ligand-bonded fiber 3).

Comparative Example 1

The fiber precursor 1 obtained in Example 1 was used as the fiber of Comparative Example 1, without immobilization of ligand compound [4].

The ligand-bonded fibers 1-3 of Examples 1-3 and the fiber of Comparative Example 1 were used together with the substrate on which the fiber precursor was formed.

Comparative Example 2

A Φ30 mm PSt substrate that underwent the above-mentioned surface treatment A was used as a substrate of Comparative Example 2.

The fiber precursor weight of each of the ligand-bonded fibers 1-3 of Examples 1-3 and the fiber of Comparative Example 1 is shown in Table 1. The fiber precursor weight of the ligand-bonded fibers 1-3 and the fiber precursor weight of the fiber of Comparative Example 1 was calculated by measuring the total weight of the fiber precursor and a PSt substrate supporting the fiber precursor, and subtracting the weight of the PSt substrate from the weight.

TABLE 1

| | surface treatment of PSt substrate | fiber precursor weight (μg) | fabric weight of fiber precursor (μg/cm$^2$) |
|---|---|---|---|
| ligand-bonded fiber 1 of Example 1 | A (Pt—Pd vapor deposition) | 920 | 130 |
| ligand-bonded fiber 2 of Example 2 | B (UV ozone) | 120 | 17 |
| ligand-bonded fiber 3 of Example 3 | untreated | 70 | 9.9 |
| fiber of Comparative Example 1 | A (Pt—Pd vapor deposition) | 990 | 140 |

[Immobilization of Ligand Compound [4]]

The fiber precursors 1-3 of Examples 1-3 were configured in 6 well flat-bottom microplates (manufactured by AS ONE Corporation). A solution of ligand compound [4] (0.9 mg) in dimethyl sulfoxide (2.0 mL) was added to the well in which each fiber precursor was configured, and the well was stood at room temperature for 6 hr. Thereafter, the solution was removed, and each fiber precursor was washed with dimethyl sulfoxide and ethanol, and air dried.

Experimental Example 1: Cell Culture Evaluation

The ligand-bonded fiber 1 of Example 1 and the fiber of Comparative Example 1 were subjected to cell culture evaluation. As a control for the evaluation, a system in which PSt substrate was configured (positive control: thrombopoietin (TPO) (10 ng/mL) was added to medium, negative control: medium alone) was used. In the following, the $CO_2$ concentration (%) of the $CO_2$ incubator is shown by % by volume of $CO_2$ in the atmosphere.

[Preparation of Cell]

As the cell, TPO-dependent human megakaryoblastic leukemia cell line (UT-7/TPO; Komatsu et. al., Blood, 1996, 87, pp. 4552-4560) was used. For cell culture, IMDM (Iscove's Modified Dulbecco's Medium) medium (manufactured by Sigma-Aldrich) containing 10% (v/v) FBS and 10 ng/mL TPO (Thrombopoietin, manufactured by Pepro-Tech) was used. The cells were cultured for not less than 2 days in a $CO_2$ incubator at 37° C. while keeping 5% carbon dioxide concentration. The obtained culture medium was centrifuged (manufactured by TOMY SEIKO Co., Ltd., LC-200, 1500 rpm/3 min, room temperature), the supernatant was removed, the above-mentioned IMDM medium free of TPO was added to prepare a cell suspension. The "FBS" here means fetal bovine serum (manufactured by Biological Industries).

[Sterilization of Substrate]

The ligand-bonded fiber of Example 1, the fiber of Comparative Example 1, and PSt substrate (for positive control and negative control) were configured in 6 well flat-bottom microplates (manufactured by AS ONE Corporation). 70% Ethanol (2 mL) was added, the microplate was immersed at room temperature for 5 min and air dried for 10 min.

[Cell Culture, First Time]

Sterilized ligand-bonded fibers 1-3 of Examples 1-3, the fiber of Comparative Example 1, the substrate of Comparative Example 2, and PSt substrates for positive control and negative control were configured in 6 well flat-bottom microplate, and washed twice with IMDM (Iscove's Modified Dulbecco's Medium) medium (manufactured by Sigma-Aldrich) (2 mL). Then, a cell suspension of UT-7/TPO prepared to $8.0 \times 10^4$ cells/4 mL/well was added. Of the wells configured with the PSt substrate, TPO was added to a well, configured with the PSt substrate for positive control, to a final concentration of 10 ng/mL. Thereafter, the mixture was stood in a $CO_2$ incubator at 37° C. for 6 days while keeping 5% carbon dioxide concentration.

[Cell Number Count Using WST-8]

After 6 days of cell culture, the cell culture medium was recovered from respective wells in which the ligand-bonded fibers 1-3 of Examples 1-3, the fiber of Comparative Example 1, the substrate of Comparative Example 2, and PSt substrates for positive control and negative control were configured. Each cell culture medium was pipetted, 100 μL thereof was transferred to a 96 well plate (manufactured by Corning Incorporated), and 10 μL of WST-8 reagent (manufactured by KISHIDA CHEMICAL Co., Ltd.) was added. After standing in a $CO_2$ incubator at 37° C. for 120 min, the absorbance at 450 nm was measured by an absorption spectrometer (manufactured by Molecular Devices, SpectraMax).

[Cell Culture, Second Time and Third Time]

After the first cell culture, the ligand-bonded fibers 1-3 of Examples 1-3, and PSt substrates for positive control and negative control were washed twice with phosphate buffered saline (PBS) (4 mL). Then, a cell suspension of UT-7/TPO prepared to $8.0 \times 10^4$ cells/4 mL/well was added. TPO was added to a well, configured with the PSt substrate for positive control, to a final concentration of 10 ng/mL. Thereafter, the mixture was stood in a $CO_2$ incubator at 37° C. for 6 days while keeping 5% carbon dioxide concentration.

After 6 days of culture, the cell number was counted in the same manner as above by using WST-8.

After the second cell culture and cell number counting, the third cell culture (6 days) and cell number counting was performed in the same manner.

The results are shown in Table 2 and Table 3. The cell number of each sample was compared by converting to percentage with the cell number of the positive control as 100%.

TABLE 2

| | cell number (%) cell culture, first time |
|---|---|
| ligand-bonded fiber 1 of Example 1 | 110 |
| fiber of Comparative Example 1 | 4 |
| substrate of Comparative Example 2 | 32 |

TABLE 3

| | cell number (%) | | |
|---|---|---|---|
| | cell culture, first time | cell culture, second time | cell culture, third time |
| ligand-bonded fiber 1 of Example 1 | 110 | 115 | 140 |

TABLE 3-continued

| | cell number (%) | | |
|---|---|---|---|
| | cell culture, first time | cell culture, second time | cell culture, third time |
| ligand-bonded fiber 2 of Example 2 | 122 | 100 | 140 |
| ligand-bonded fiber 3 of Example 3 | 7 | 2 | 3 |
| positive control | 100 | 100 | 100 |
| negative control | 0 | 7 | 1 |

As is clear from the results shown in Table 3, a cell number equivalent to or not less than that of the positive control was obtained in the ligand-bonded fibers of Example 1 and Example 2. It is considered that, since the amount of the fiber precursor contained was larger than that of the ligand-bonded fiber of Example 3, many ligands could be immobilized, as a result of which, signal transduction necessary for cell proliferation was actively performed.

Also, in the ligand-bonded fibers of Example 1 and Example 2, since the ligand was immobilized on the fiber precursor, the equivalent number of cells was obtained each time when the cell culture was repeated. In contrast, the positive control required addition of TPO each time the cell culture was repeated.

Furthermore, when the fiber diameter of the ligand-bonded fiber was not less than 100 nm, and the fabric weight of the fiber precursor in the substrate was 10 μg/cm² or more, more preferably 13 μg/cm² or more, most preferably 15 μg/cm² or more, a cell number equivalent to or not less than that of the positive control was obtained.

INDUSTRIAL APPLICABILITY

According to the present invention, a ligand-bonded fiber, in which a ligand is immobilized on a fiber precursor, can be provided, and the ligand-bonded fiber can efficiently and repeatedly proliferate only the objective cell, and expresses superior function as a cell culture substrate conventionally absent in the field of regenerative medicine.

This application is based on a patent application No. 2014-223736 filed in Japan (filing date: Oct. 31, 2014), the contents of which are incorporated in full herein.

The invention claimed is:

1. A ligand-bonded fiber comprising a ligand having affinity for a cell membrane receptor, and a fiber precursor bonded to the ligand,
    wherein
    the cell membrane receptor is a thrombopoietin (TPO) receptor and
    the fiber precursor comprises a polymer compound comprising
    (a) a unit structure represented by formula (1):

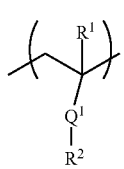

(1)

wherein
    $R^1$ is a hydrogen atom or a methyl group,
    $Q^1$ is an ester bond or amide bond,
    $R^2$ is an alkyl group having 1-10 carbon atoms or an aromatic hydrocarbon group having 6-10 carbon atoms, wherein at least one hydrogen atom is substituted by a hydroxy group, and
    (b) a unit structure represented by formula (2):

(2)

wherein
    $R^3$ is a hydrogen atom or a methyl group, and
    $Q^2$ is an active ester group.

2. The ligand-bonded fiber according to claim 1, wherein the ligand has an amino group, and the amino group is bonded to the fiber precursor through the active ester group $Q^2$.

3. The ligand-bonded fiber according to claim 1, wherein $Q^2$ is represented by formula (3):

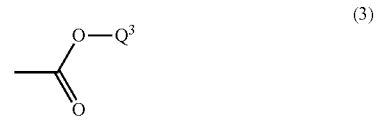

(3)

wherein $Q^3$ is an N-succinimide group, a p-nitrophenyl group or a pentafluorophenyl group.

4. The ligand-bonded fiber according to claim 1, wherein the fiber precursor further comprises a crosslinking agent and an acid compound.

5. The ligand-bonded fiber according to claim 1, wherein the fiber precursor is produced by spinning a composition for producing a fiber precursor, which composition comprising the polymer compound, a crosslinking agent, an acid compound and a solvent.

6. The ligand-bonded fiber according to claim 5, wherein the fiber precursor is produced by spinning the composition for producing a fiber precursor, on a surface-treated substrate.

7. The ligand-bonded fiber according to claim 1, wherein the polymer compound has a weight average molecular weight of 1,000-1,000,000.

8. The ligand-bonded fiber according to claim 1, wherein the fiber precursor is produced by heating at 70-300° C.

9. The ligand-bonded fiber according to claim 1, wherein the ligand is a compound represented by formula (4):

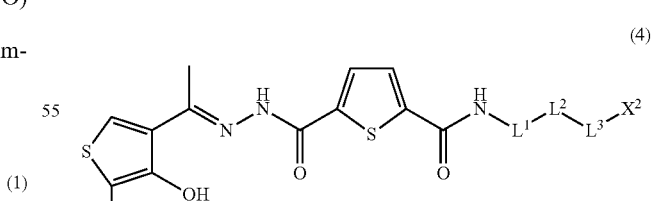

(4)

wherein
    $X^1$ is a 3,4-dichlorophenyl group, a 4-trifluoromethylphenyl group or a 4-t-butylphenyl group,
    $X^2$ is an optionally substituted amino group,
    $L^1$ is a single bond or $-CH_2-C_6H_4-$,
    $L^2$ is a single bond or $-CONH-$, and
    $L^3$ is an alkylene group having 2-6 carbon atoms.

10. The ligand-bonded fiber according to claim 9, wherein $X^1$ is a 4-t-butylphenyl group, and $X^2$ is an amino group.

11. A cell culture substrate comprising the ligand-bonded fiber according to claim 1.

12. The ligand-bonded fiber according to claim 4, wherein the fiber precursor is produced by heating at 70-300° C.

13. The ligand-bonded fiber according to claim 4, wherein the ligand is a compound represented by formula (4):

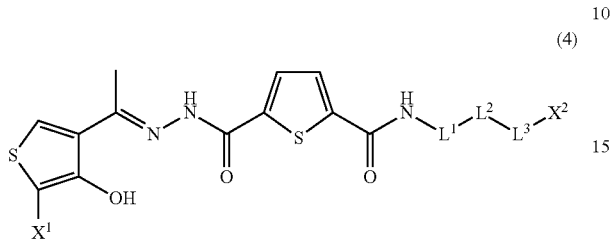

wherein
$X^1$ is a 3,4-dichlorophenyl group, a 4-trifluoromethylphenyl group or a 4-t-butylphenyl group,
$X^2$ is an optionally substituted amino group,
$L^1$ is a single bond or —$CH_2$—$C_6H_4$—,
$L^2$ is a single bond or —CONH—, and
$L^3$ is an alkylene group having 2-6 carbon atoms.

14. The ligand-bonded fiber according to claim 13, wherein $X^1$ is a 4-t-butylphenyl group, and $X^2$ is an amino group.

15. A cell culture substrate comprising the ligand-bonded fiber according to claim 4.

* * * * *